United States Patent [19]
Zakoshansky et al.

[11] Patent Number: 5,530,166
[45] Date of Patent: Jun. 25, 1996

[54] METHOD OF TECHNICAL CUMENE HYDROPEROXIDE ACIDIC CLEAVAGE TO PHENOL, ACETONE AND ALPHA-METHYLSTYRENE

[75] Inventors: Vladimir M. Zakoshansky; Andrei K. Griaznov, both of St. Petersburg, Russian Federation

[73] Assignees: General Electric Company, Pittsfield, Mass.; Illa International, St. Petersburg, Russian Federation

[21] Appl. No.: 369,104

[22] Filed: Jan. 13, 1995

[30] Foreign Application Priority Data

Mar. 1, 1994 [RU] Russian Federation ............. 94007336

[51] Int. Cl.⁶ ................................................. C07C 37/08
[52] U.S. Cl. .......................................... 568/798; 568/385
[58] Field of Search ................................... 568/735, 798, 568/385

[56] References Cited

U.S. PATENT DOCUMENTS

| | | | |
|---|---|---|---|
| 5,245,090 | 9/1993 | DeCaria et al. | 568/798 |
| 5,254,751 | 10/1993 | Zakoshansky | 568/798 |
| 5,264,636 | 11/1993 | Shirahata et al. | 568/754 |
| 5,371,305 | 12/1994 | Hood | 568/798 |

*Primary Examiner*—Werren B. Lone

[57] ABSTRACT

Technical cumylhydroperoxide of a wide composition range is cleaved in circulating reactors of a shell and tube design at the same elevated pressure as dicumyl peroxide is cleaved in a plug flow reactor with a recirculation ratio of at least 26. The cleavage process is controlled using two calorimeters and controlling the absolute ΔT value which is the difference in the temperature drop between the two calorimeters.

12 Claims, 2 Drawing Sheets

METHOD OF TECHNICAL CUMENE HYDROPEROXIDE ACIDIC CLEAVAGE TO PHENOL, ACETONE AND ALPHA-METHYLSTYRENE

This invention relates to the synthesis of phenol, acetone and alpha-methylstyrene (AMS) the cumene method.

The cumene method comprises two stages: the first one is cumene oxidation by air oxygen to cumene hydroperoxide (CHP), the second one is CHP acidic-catalytic cleavage (decomposition) to phenol and acetone. During CHP cleavage some unutilized products known as "phenol tar" form along with the phenol, acetone and AMS. The phenol tar amount is mostly determined by the method of implementing the CHP cleavage process and makes 50–60 kg/t in the best current technologies and over 120–180 kg/t of phenol in traditional technology.

Up to now the efforts of skilled artisans were directed to increasing the process selectivity or yield. However, along with selectivity, the process throughput or rated capacity is also an important factor in measuring the overall productivity of a phenol-acetone production unit. Up until now it was impossible to meet both of these requirements simultaneously.

Figure 1:
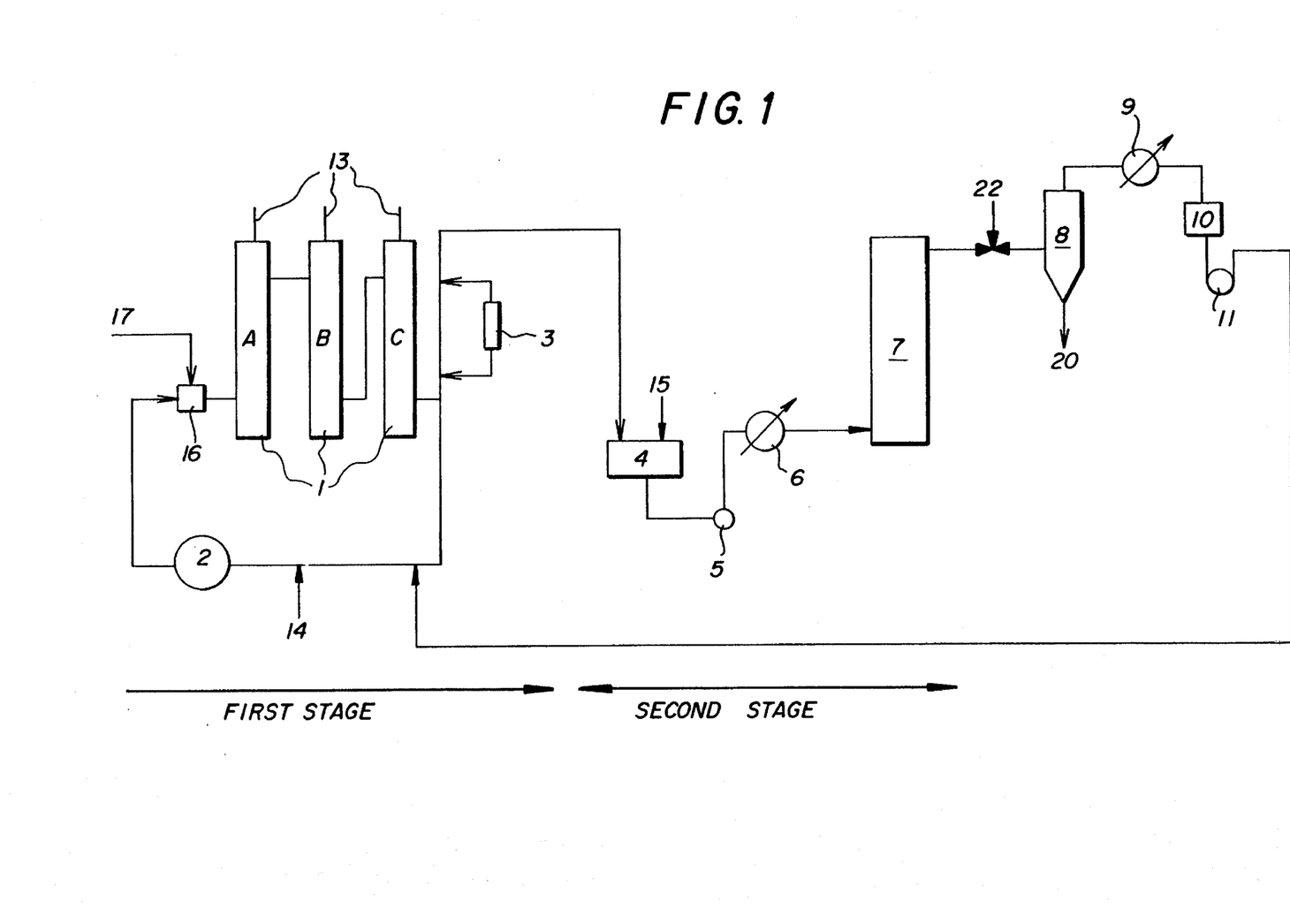

The most recent technical advance is based on the CHP cleavage method disclosed in U.S. Pat. No. 5,254,751. Technical CHP cleavage is carried out in accordance with this process as set forth in FIG. 1. This process is carried out in two stages:

The first stage is the CHP cleavage stage catalyzed by sulfuric acid which is carried out in three shell and tube type reactors A, B and C, installed in series, with reaction heat removal by cooling water fed to the reactors' tube space and cleavage products circulating through the reaction unit with a ratio of 10–25/1 for recirculation weight to weight of CHP fed. The sulfuric acid catalyst is most conveniently supplied to the reactors by adding it to the recirculated cleavage products through line 14. Pump 2 moves the recirculated cleavage products and sulfuric acid catalyst to mixer 16 into which fresh technical CHP is added through line 17 from which the mixture moves to reactor A. In order to increase process selectivity an additional amount of water and acetone is fed to the circulating cleavage stream. Acetone is fed by the following algorithm (I) depending upon the loading of CHP.

$$Gac = G_{CHP} \times 0.17[CHP] + \frac{40}{G_{CHP}[CHP]}$$

where: Gac—acetone amount, t/hr
$G_{CHP}$—technical CHP amount. in t/hr
[CHP]—CHP concentration in technical CHP by weight In establishing each of the algorithms set forth in this specification the amounts were measured in terms of metric tons (ton or t). However, any weight quantity measurement may be employed so long as the same selected quantity units are used consistently for each component.

Technical CHP is known to the skilled artisan as impure cumylhydroperoxide containing varying amounts of impurities such as DMBA, cumene, AP and other similar materials which is the product stream from cumene oxidation which is the initial step in the phenol from cumene manufacturing process.

The technique of recycling acetone is very important to provide process selectivity which is determined by closely controlled temperature ranges in each of the three reactors (A, B and C of process section 1 of the first stage of the process) as 50°–62° C., 62°–57° C. and 57°–50° C. respectively at atmospheric pressure and CHP conversions in each of the reactors 30–60%. 25–50% and 30–10% respectively. Reactors A, B and C are vented to the atmosphere through appropriately designed vents 13.

As the reaction of CHP cleavage is highly exothermic, reactors with a total specific heat exchange area of not less than 30–35 m$^2$ per metric ton of 100% CHP are used. Because of the potential danger of the CHP cleavage reaction it is safer practice to design reactors with a specific area not less than 45–60 m$^2$ per metric ton of fed 100% CHP.

On-line monitoring of the progress of CHP decomposition in the first stage is carried out by a specially designed calorimeter (mini-reactor) 3 installed on the outlet line of the last reactor. The temperature difference between the calorimeter inlet and outlet streams (delta $T_1$) is a quantitative measure of the amount of undecomposed CHP remaining in the cleavage product stream. A typical delta $T_1$ is 4°–16° C. which corresponds to 0.6 to 2.3 wt % of free CHP exiting the last reactor of stage 1 of the process. Also during cleavage of CHP, the dimethylbenzyl alcohol (DMBA) impurity present in the technical CHP feed stream simultaneously reacts in part with CHP to form the intermediate dicumylperoxide (DCP).

The CHP cleavage time is varied from 30 seconds to 3 minutes, preferably 45 sec.–2 min., within the above mentioned ranges for circulation ratio and CHP conversion.

The second stage, DCP cleavage, is carried out subsequently in two apparatuses 4 and 7 which are plug flow reactors. Aqueous ammonium hydroxide solution is fed through line 15 to the first of the reactors 4 to convert part of the sulfuric acid to $NH_4HSO_4$. Thus DCP cleavage is carried out with a binary catalyst ($H_2SO_4+NH_4HSO_4$) with a controlled ratio of the components and at a temperature of 90°–110° C. in apparatus 7. Product heating is implemented by heat exchanger 6.

CHP cleavage in reactors A, B, and C of process section 1 is carried out under atmospheric pressure and are vented to the atmosphere through appropriately designed vents 13. DCP cleavage in reactor 4 is carried out under atmospheric pressure and in reactor 7 under pressure of not less than 2 atm. Between reactor 7 and evaporator 8 is a pressure reduction valve 22.

A portion of the acetone in the cleavage products is evaporated in evaporator 8 at about atmospheric pressure or below and preferably at between about 500–600 mm Hg absolute. The remainder of the cleavage products leave evaporator as a bottoms stream and move through line 20 for further processing into product phenol and product acetone. The evaporated acetone is cooled and condensed to the liquid state in cooler 9. The liquid acetone is fed to vessel 10 before being pumped through pump 11 to reactors A, B and C in process section 1.

The above described method gives the highest levels of process selectivity up to the present invention. But it has a few areas which can be substantially improved:

1) Big volume reactors are required to provide the substantial amount of heat exchange (more than 50 m$^2$/t. of 100% CHP) which leads to high equipment cost and high capital investment for construction and surge capacities of unit;

2) The intermediate vessel (reactor 4) operates under atmospheric pressure and pump 5 is required to deliver the cleavage mass to the downstream DCP conversion reactor 7 in the second stage of the process.

3) The reduced temperature in CHP cleavage process section I allows a high level of nondecomposed CHP (from 0.5 to 2%) in reactor 4 which, if there is a wrong ratio between $H_2SO_4$: $NH_4HSO_4$, could result in a hazardous condition.

4) Precise dosing of small amounts of aqueous ammonia solutions and $H_2SO_4$ to maintain the correct ratio is difficult and lack of precision leads to AMS dimers and formation of phenol complexes, in case of low $H_2SO_4$ neutralization, or to incomplete DCP conversion in case of over neutralization of $H_2SO_4$. Desired products yield is reduced in both cases and "phenol tar" yield increases accordingly.

5) $H_2SO_4$ and $NH_4HSO_4$ presence in cleavage products causes the acidic-catalytic properties of these catalysts to increase by 4–7 times and their concentration to increase simultaneously in vessel 8 during acetone evaporation. Side reactions continue in this vessel and by-product formation reduces process selectivity. The above mentioned low dosing of $NH_4OH$ aggravates this situation leading to a loss of 10–20 kg. of starting cumene feed on the basis of 1 ton of phenol and AMS yield can be reduced to as low as 60% theoretical.

6) Operating the DCP cleavage reactor 7 with a very weak acidic catalyst ($H_2SO_4+NH_4HSO_4$) requires a high reactor volume, 0.8 m³/t of feed to the reactor which unfavorably compares with 0.4–0.5 m³/t of feed in the process of the present invention.

7) Acetone feed to the CHP cleavage unit by the above algorithm (I) leads to high energy requirements for its condensation and requires apparatus with increased heat exchange capacity which also leads to high costs for equipment sized to accommodate surge.

In contrast, the present invention increases productivity of the process units, reduces capital investment through equipment volume reduction in new units being constructed and simplifies the technology but maintains high process selectivity.

A BRIEF DESCRIPTION OF THE DRAWING

The process of the prior art is represented in FIG. 1.

The process of the present invention is represented in FIG. 2.

Figure 2:
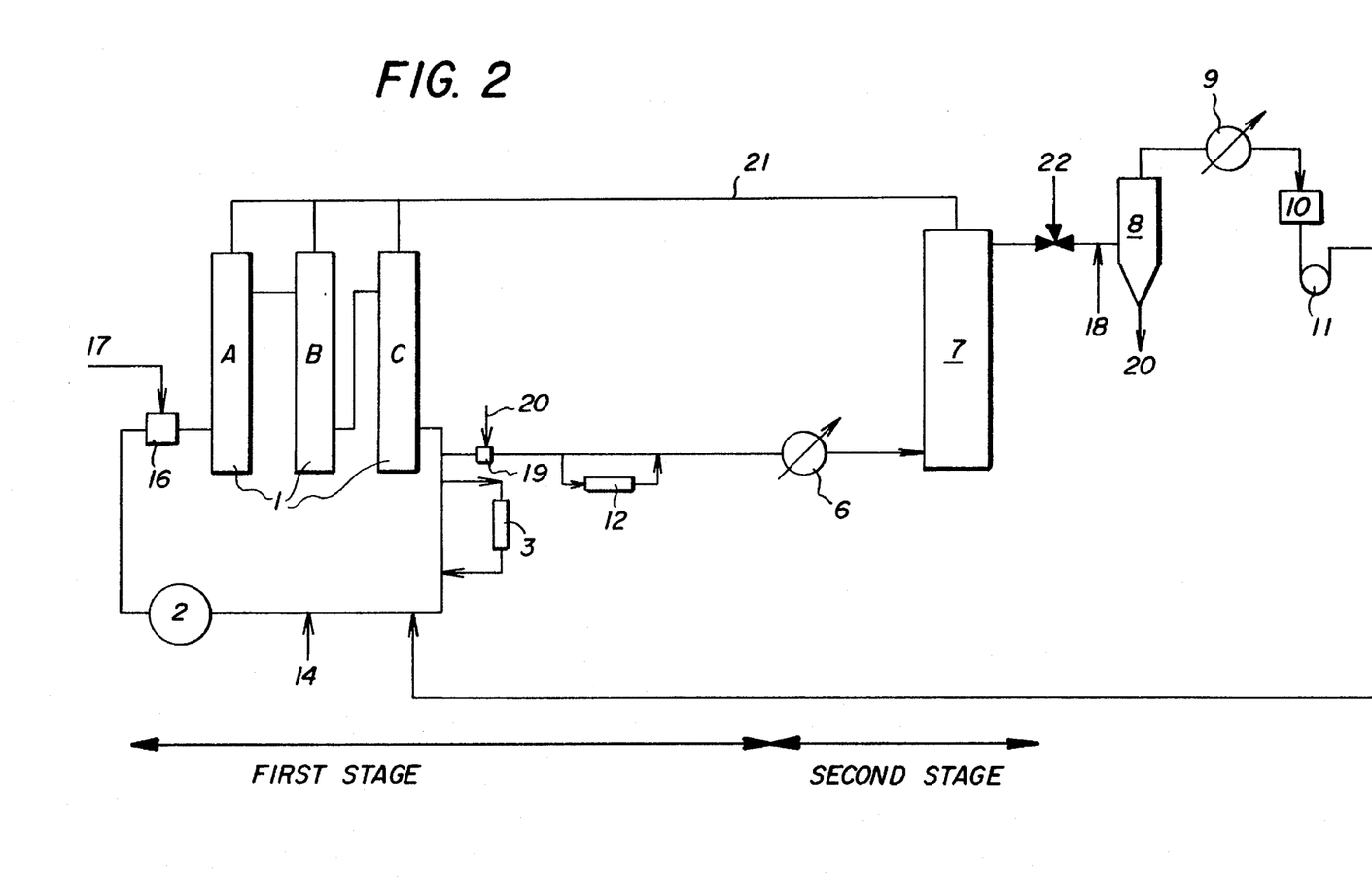

In the process of this invention, CHP and DCP cleavage stages are carried out in reactors connected in series under the same pressure. The CHP feed stream is fed into a circulating loop of the products of the cleavage reaction containing sulfuric acid catalyst. As in the prior art process, the sulfuric acid catalyst is conveniently added to the circulating loop through line 14 and technical CHP is added through line 17 and mixed with the recirculating CHP cleavage mass in mixer 16. Although in the prior art process reactors A, B and C are vented to the atmosphere, in the process of the present invention line 21 connects the overheads of reactors A, B, C and 7 together to keep all reactors at the same elevated pressure. Since all four reactors, A, B, C and 7, are at the same pressure, and reactor 4 has been eliminated in the process of the present invention, the aqueous ammonia solution, fed to the prior art process shown in FIG. 1 through line 15, is fed to the line feeding evaporator 8 after the pressure reducing valve 22 in the process of the present invention. Although it is most convenient to add the aqueous ammonia immediately before evaporator 8 as shown in FIG. 2 and be certain no ammonia is present in reactor 7, the point of addition after reactor 7 whether before or after valve 22 is not critical so long as no ammonia is present in reactor 7.

In the present invention this investment in pumps and reactor 4 is not required since both the first and second stages of the process are designed to operate at identical elevated pressures. The first stage reactors in the present invention operate at a higher temperature than in the prior art method and this higher temperature requires the use of a higher pressure to suppress the boiling point of the cleavage mass. This higher pressure in the first stage of the process of the present invention is the same as the pressure in the second stage thus eliminating the need for pumps.

As cleavage of CHP occurs, the heat liberated is removed by cooling water in reactors A, B and C of process section 1 of the first stage of the process. The weight ratio of reactor circulation rate to CHP feed rate is not less than about 26:1 but not more than about 40:1, preferably about 26:1 to about 35:1.

According to the process of the present invention, acetone is fed to reactor A of process section 1 of the first stage of the process and its ratio is determined depending on technical CHP amount fed for cleavage by the following algorithm (II):

$$G_{ac} = G_{CHP} \times 0.125[CHP] + \frac{35}{G_{CHP}[CHP]}$$

where: $G_{ac}$—acetone amount fed for cleavage in t/hr
$G_{CHP}$—technical CHP amount fed for cleavage, t/hr
[CHP]—CHP concentration in technical CHP by weight.

This algorithm is suitable for most currently available technical CHP streams, e.g. having a CHP concentration of from about 74 percent by weight to about 92 percent by weight.

A broader algorithm which has a broader range of applicability has been discovered and provides a basis for controlling the process employing a wider range of technical CHP feedstocks.

This algorithm (III) is as follows:

$$G_{ac} = 0.58 G_{CHP} \times \left( \frac{1.315[CHP]}{50 + 0.25[CHP]} - \frac{2[CHP]}{152} - \frac{[DMBA]}{136} - \frac{[cumene]}{120} - \frac{[AP]}{120} \right)$$

where: $G_{ac}$—acetone amount fed for cleavage in t/hr
$G_{CHP}$—technical CHP amount fed for cleavage in t/hr
[CHP]—CHP concentration in technical CHP by weight.
[DMBA]—DMBA concentration in technical CHP by weight
[Cumene]—Cumene concentration in technical CHP by weight
[AP]—Acetophenone (AP) concentration in technical CHP by weight This algorithm expands the application of the present invention to streams having a CHP concentration as low as 40 percent by weight CHP and as high as about 98% by weight CHP, preferably about 50 percent to about 90 percent and more preferably about 60 percent to about 85 percent. However, this algorithm can be used in a process employing any level of CHP concentrations.

In the present invention, higher temperatures and higher conversion rates of CHP are employed in the first stage of the CHP decomposition process. The conversion profile of reactors A, B and C is controlled respectively at: 55–78%; 60–94%; and 90–98%, respectively. Overall conversion of CHP may be nearly complete in the present invention. A calorimeter (mini-reactor) 3 is installed on the outlet of the reactor C to indicate overall degree of CHP conversion via the delta $T_1$ signal described earlier. A typical value for delta $T_1$ is from about 0.4° to about 2.1° C. A typical temperature profile for reactors A, B and C is: 57°–82° C., 65°–82° C.

and 57°–70° C. at a pressure of from about 3 to about 4 atmospheres.

The CHP concentration at reactor C outlet is held at a 0.1–0.45 wt % and preferably 0.2–0.4 wt % and CHP cleavage time from 17 to 28 sec. Reactors with heat exchange total specific area of 17–25 m²/t. of 100% CHP are used in the process of the present invention.

The cleavage mass from reactor C is fed to reactor 7 through heater 6 where conversion of DCP and DMBA to desired products is carried out.

Water in an amount sufficient to provide 98% DCP and DMBA conversion in reactor 7 is fed through line 20 to static mixer 19 in the product line exiting reactor C. The water content in the cleavage products is controlled so as not to exceed 3 wt % and preferably 1.3–2.0 wt %.

Control of the extent of DCP and DMBA decomposition after the point of water mixing with the cleavage products is accomplished by on-line monitoring the temperature difference (delta $T_2$) of a second mini-reactor (calorimeter) 12 installed in parallel to the line connecting reactors A, B and C of process section 1 of the first stage of the process to reactor 7. The temperature in mini-reactor 12 is controlled at both its inlet and outlet.

The design of calorimeter 12 is not critical so long as the residence time of the cleavage products in the calorimeter 12 is sufficient for total conversion of DCP and DMBA into phenol, acetone and AMS. Typically, this is achieved by a low flow of the cleavage products slipstream.

Temperature control of the process is carried out through the temperature difference (delta T) which is the difference between the delta $T_1$ of the first calorimeter and the delta $T_2$ of the second calorimeter. This delta T absolute value is held in a range of 0.2°–3° C.

To exclude chemical losses during acetone evaporation at the product inlet to evaporator 8, a neutralizing alkaline agent is fed through line 18 in an amount necessary to totally neutralize $H_2SO_4$ into neutral salts (sulfates). $Na_2CO_3$, $NH_4OH$, NaOH may be used as the neutralizing agent, but an aqueous ammonia solution of from 1 to 10 wt % concentration is preferable.

The process of the present invention provides the following benefits:

1) More forgiving process which can utilize a broader range of CHP concentration in technical CHP (40–98% by weight) at a high level of process efficiency.

2) Equipment productivity increases 2–2.5 times without substantial capital investment. In spite of high process throughput, selectivity stays maximal (AMS yield is 78–80% theoretical);

3) Investment in a new cleavage unit to be constructed is reduced by 50 to 60 percent because:

a) The CHP cleavage reaction takes place in reactors with a low specific heat exchange area (17–25 m²/t. of CHP) compared to traditional reactors with a specific heat exchange area of 40–60 m²/t. of CHP;

b) The DCP cleavage reaction takes place in one reactor instead of two. The two reactors may be integrated to one unit because both reactors operate under the same pressure;

4) Energy consumption for process operation is lowered by the reduction of the recycled acetone amount and elimination of pump 5 from the process scheme.

5) Elimination of the ammonia feed stream to the DCP cleavage step and addition of only water simplifies the control of the acidic-catalytic properties of $H_2SO_4$.

6) CHP cleavage process is simplified by process control through delta T=delta $T_2$–delta $T_1$ which helps to maintain process selectivity automatically at the CHP cleavage stage and at the DCP cleavage stage as well.

7) Complete $H_2SO_4$ neutralization before the acetone evaporator helps to exclude undesired side reactions.

In addition, emission sources of low boiling acetone in the prior art process are eliminated by connecting reactors A, B and C of process section 1 and the DCP cleavage reactor in the process embodying this new technology.

The present invention is illustrated but not limited by the following is Examples 2–14 as compared to comparative Example 1 which represents the prior art.

COMPARATIVE EXAMPLE 1

Using the prior art process described in FIG. 1, technical CHP of the following composition in % wt is fed continuously to a reactor block consisting of three shell and tube reactors which have a total reaction volume 10.08 m³:

| | |
|---|---|
| cumene hydroperoxide | 82.500% by weight |
| cumene | 12.721% by weight |
| dimethylbenzyl alcohol | 4.325% by weight |
| acetophenone | 0.453% by weight |

26 tons per hour of technical CHP are fed to CHP reactors A, B and C. Based upon calculations using algorithm (I), 5492 kg/h of acetone is added. 16 kg/h of sulfuric acid are fed to this reactor where the cleavage products are recirculating. For the cleavage reaction, the reactors have a total heat transfer surface 1254 m² that corresponds to the value of the specific heat transfer, which makes 58 m²/t of CHP for each ton of 100% CHP.

The residence time in the reactor of CHP cleavage is 74 sec. The temperatures at the output line from each reactor is, respectively, 58° C., 55° C. and 50° C. The CHP conversion at the output from each reactor is, respectively, 38%, 73%, 85%. The value of the temperature drop (delta $T_1$) in the mini-reactor 3 is 5.6° C. The CHP mixes with the reactive cleavage mass at the cleavage reactor inlet in a ratio of 1:16 (the circulation ratio is 16). 10 kg of sulfuric acid is added to the circulating loop.

DCP cleavage is carried out in two plug flow reactors working in succession with a low temperature in the first reactor, which is 58° C., and 93° C. in the second reactor. 33.8 kg/h of an aqueous ammonia solution at a concentration of 5% wt is fed to the first reactor, so that the degree of sulfuric acid neutralization for the conversion of the latter into ammonia bisulfate would be 50%.

The CHP cleavage in the three shell and tube reactors and the DCP cleavage in the two plug flow reactors are carried out at different pressures; atmospheric pressure in the CHP cleavage reactors and in the first reactor of the DCP cleavage and 3–5 atm in the second reactor of the DCP cleavage.

The residence time in the DCP cleavage reactors is 420 sec in reactor 4 and 2030 sec in reactor 7.

Acetone is fed to the cleavage unit from vessel 10 by pump 11. This acetone is evaporated from the reactive cleavage mass of DCP under reduced pressure in evaporator 8 and condensed to liquid in cooler 9.

As a result of all the reactions, which occur in the reactors, one gets:

phenol—13174.5 kg/h (yield 99.2%)

acetone—8084.5 kg/h (yield 98.9%)

alphamethylstyrene—54.5 kg/t. of phenol (the yield of AMS is 73.4 theoretical % taking into consideration the fed DMBA)

yield of phenol tar—59.2 kg/t of phenol cumene consumption—1333 kg per ton of phenol The cumene consumption values in this example and the subsequent examples are presented only for purposes of comparison of the effectiveness of the process of the present invention which relates only to a portion of the total phenol process. When other cumene recovery operations, not a part of the present invention, are included in the measurement of cumene consumption in the total process, the net cumene consumption is much lower, typically 1307–1310 kg per ton.

EXAMPLE 2

This example of the present invention shows an increase in productivity of 2.3 times over example 1. The process of the present invention as described in this example and in the following examples is carried out as described in FIG. 2. All the reactors of the present example operate under the same pressure and the pressure under which the entire system operates is 4 kg/cm².

60 tons per hour of technical CHP are fed to the CHP cleavage reactors. The composition is the same as in Example 1. The cleavage of technical CHP is carried out at a recirculating ratio of 26/1 at temperatures at the inlet of each reactor of 68° C., 67° C. and 60° C. respectively with a cumulative CHP conversion in each reactor of 62%, 94%, 98% respectively.

Condensed acetone from vessel 10 is fed to the cleavage unit (process section 1) at a rate of 6890 kg/h calculated by the formula (II):

$$G_{ac} = G_{CHP} \times 0.125[CHP] + \frac{35}{G_{CHP}[CHP]}$$

where $G_{ac}$, is the amount of acetone and $G_{CHP}$ is the amount of technical CHP, both of which are expressed in tons per hour. As used herein a ton (t) is equal to 1000 kilograms (kg).

[CHP] is the CHP concentration in technical hydroperoxide expressed as % wt. In the mini-reactor 3 of the cleavage unit the value of the temperature drop is a delta $T_1 = 0.4°$ C.

Through the line feeding into the DCP cleavage reactor 7, water is fed at the rate of 482 kg/h so that the concentration of the water in the cleavage products at the reactor outlet will be 1.63 wt % and the cleavage time is 485 seconds.

At the point after mixing cleavage products with water a second mini-reactor (calorimeter) 12 is installed where the value of the drop of temperatures (delta $T_2$) at the outlet and at the inlet is measured. The process control essentially is carried out by means of the value of the absolute temperature drop delta $T$ = delta $T_2$ – delta $T_1$ = 0.65° C.

To the product inlet line into the acetone evaporator 8 an aqueous ammonia solution at a concentration of 10% wt and at the rate of 145 kg/h is fed through line 18 to exclude chemical losses of desired products in the acetone evaporator 8.

As a result one gets:
phenol—30431.2 kg/h (yield 99.5%)
acetone—18769.7 kg/h (yield 98.5%)
alphamethylstyrene—58.5 kg/t. of phenol (the yield of AMS is 79.9 theoretical % taking into consideration the fed DMBA)
yield of phenol tar—54.2 kg/t of phenol
cumene consumption—1328 kg per ton of phenol

EXAMPLE 3

This example shows conducting the process of the invention in reactors A, B and C of reduced volume with reduced heat transfer surface and consequently with low specific surface of heat transfer. This process is carried out according to the scheme described in Example 2. However, for the apparatus used in Example 3:

the volume of the reactor system of CHP cleavage is 2.8 times less than Example 1, the surface of heat transfer of this system is 3.5 times less than in Example 1 and the specific surface of heat exchanger of DCP cleavage is 3 times less than analogous values described in Example 1.

26 tons per hour of technical CHP, which has the same composition as defined in Example 1, is fed to the CHP cleavage reactors. To the recirculating loop which consists of the CHP cleavage reactors (A, B and C of process section 1) 9.3 kg/h of sulfuric acid is fed. The cleavage of technical CHP is carried out at the temperatures at the reactors' A, B and C outlet which are 79° C., 75° C. and 69° C. respectively and with CHP conversion which is 77%, 96%, 98% respectively.

Recycle acetone at the rate of 4312 kg/h calculated by formula II which was presented in Example 2, is fed to the CHP cleavage unit from the vessel 10.

The residence time of reaction products in the DCP cleavage reactor 7 is 638 seconds.

As a result one gets:
phenol—13185.3 kg/h (yield 99.4%)
acetone—8075.4 kg/h (yield 98.8%)
alphamethylstyrene—58.02 kg/ton of phenol (the yield of AMS 79.9 theoretical % taking into consideration the fed DMBA)
yield of phenol tar—55.03 kg/t of phenol
cumene consumption—1329 kg per ton of phenol In the mini-reactor 3 of the cleavage unit the value of the temperature drop delta $T_1 = 0.34°$ C.

The value of the absolute temperature difference delta $T$ = delta $T_2$ – delta $T_1 = 0.66°$ C.

To the product inlet line of the acetone evaporator 8 the aqueous ammonia solution at a concentration of 10% wt and at the rate of 63 kg/h is fed to exclude chemical losses of desired products in the acetone evaporator so that the degree of the conversion of acid into ammonium sulfate in the acetone evaporator 8 is 100%.

EXAMPLE 4

This example illustrates implementation of the present invention in reactors A, B and C where the heat exchange specific area is determined to be 25 m² per ton of 100% CHP.

26 tons per hour of technical CHP, which has the composition defined by Example 1, is fed to the CHP cleavage reactors. Circulation ratio is 26/1. To the recirculation loop which consists of the reactors A, B and C of CHP cleavage 9.3 kg/h of sulfuric acid is fed. The cleavage of technical CHP is carried out at temperatures at the reactors A, B and C outlet which are 67° C., 66° C. and 61° C. respectively and at the CHP conversion which are 62%, 87%, 94% respectively.

The recycle acetone at the rate of 4312 kg/h calculated by the formula II which was presented in Example 2, is fed to the cleavage unit of CHP from vessel 10.

The residence time of reaction products in the DCP cleavage reactor 7 is 640 seconds.

As a result the following amounts are produced:

phenol—13188.5 kg/h (yield 99.3%)

acetone—8078.9 kg/h (yield 98.8%)

alphamethylstyrene—58.5 kg/ton of phenol (the yield of AMS is 79.9% theor. taking into consideration DMBA supply)

yield of phenol tar—53.9 kg/t of phenol cumene consumption—1328 kg per ton of phenol In the mini-reactor 3 of the cleavage unit the value of the temperature drop delta $T_1=1.26°$ C. The value of the temperature drop in mini-reactor 12 installed after water supply to reaction products at circulation loop outlet is 1.98° C.

Absolute temperature difference (delta T=delta $T_2$–delta $T_1$) is 0.72° C.

To the product inlet line into the acetone evaporator 8 the aqueous ammonia solution at a concentration of 10% wt and at the rate of 63 kg/h is fed through line 18 to exclude chemical losses of desired products in the acetone evaporator 8 so that the degree of the conversion of acid into ammonium sulfate in the acetone evaporator is 100%.

EXAMPLE 5

This example illustrates the high selectivity of the process of the present invention at a lower rate of feed of technical CHP per cleavage unit and a high circulation ratio.

22 tons per hour of technical CHP, which has the composition defined by Example 1, are fed to the CHP cleavage reactors. Circulation ratio is 35. To the recirculation loop which consists of the CHP cleavage reactors A, B and C, 7.2 kg/h of sulfuric acid is fed. The cleavage of technical CHP is carried out at the reactor A, B and C outlet temperatures which are 72° C., 78° C. and 67° C. respectively and at the CHP conversion which is 65%, 92%, 97% respectively.

Recycle acetone at a rate of 4192 kg/h calculated by the formula II which was presented in Example 2, is fed to the cleavage unit of CHP (process section 1) from the vessel 10.

The residence time of reaction products in the DCP cleavage reactor 7 is 865 seconds.

In the mini-reactor 3 of the cleavage unit the value of the temperature drop delta $T_1=0.82°$ C. The temperature drop in the mini-reactor 12 installed after the water supply to reaction products circulation loop outlet is 1.68° C.

Absolute temperatures difference (delta T=delta $T_2$–delta $T_1$) is 0.86° C.

To the product inlet line into the acetone evaporator 8, an aqueous ammonia solution at the concentration of 10% wt and at the rate of 48 kg/h is fed to exclude chemical losses of desired products in the acetone evaporator so that the degree of the conversion of acid into ammonium sulfate in the acetone evaporator 8 is 100%.

As a result the following amounts are produced:

phenol—11156.4 kg/h (yield 99.4%)

acetone—6815.7 kg/h (yield 98.5%)

alphamethylstyrene—58.1 kg/ton of phenol (the yield of AMS is 79.9% theoretical taking into consideration DMBA supply)

yield of phenol tar—55.14 kg/t of phenol cumene consumption—1328 kg per ton of phenol.

EXAMPLE 6

This example illustrates high selectivity of the process of the present invention at an intermediate rate of feed of technical CHP per cleavage unit.

35 tons per hour of technical CHP, which has the composition defined by Example 1 are fed to the reactors of CHP cleavage. Recirculation ratio is 26. To the recirculation loop which consists of the CHP cleavage reactors 11.80 kg/h of sulfuric acid is fed. The cleavage of technical CHP is carried out at the reactors A, B and C outlet temperature which are 74° C., 71° C. and 65° C. respectively and at the CHP conversion which makes 70%, 93%, 97% respectively.

The recycle acetone at the rate of 4821 kg/h calculated by the formula II which was presented in Example 2, is fed to the CHP cleavage unit (process section 1) from vessel 10.

The residence time of reaction products in the DCP cleavage reactor 7 is 487 seconds.

In the mini-reactor 3 of the cleavage unit the value of the temperature drop delta $T_1=0.64°$ C. The value of the temperature drop in the mini-reactor 12 installed after the supply of water to the reaction products at the circulation loop outlet is 1.92° C.

The absolute temperature difference (delta T=delta $T_2$–delta $T_1$) is 1.27° C.

To the product inlet line into the acetone evaporator 8 the aqueous ammonia solution at a concentration of 10% wt and at the rate of 80 kg/h is fed through line 18 to prevent chemical losses of desired products in the acetone evaporator so that the degree of the conversion of acid into ammonium sulfate in the acetone evaporator is 100%.

As a result the following amounts are produced;

phenol—17751 kg/h (yield 99.4% )

acetone—10906 kg/h (yield 98.5% )

alphamethylstyrene—58.6 kg/t. of phenol (the yield of AMS is 79.9% theor. taking into consideration DMBA supply)

yield of phenol tar—54.14 kg/t of phenol cumene consumption—1328 kg per ton of phenol.

EXAMPLE 7

This example illustrates the reproducibility of high selectivity of the process at an intermediate feed rate of technical CHP per cleavage unit. In this example the concentration of CHP in the technical CHP is substantially higher than in Comparative Example 1 and Examples 2–6.

35 tons per hour of technical CHP, which has the following composition are fed to the CHP cleavage reactors:

| CHP | 91.5% by weight |
|---|---|
| Cumene | 2.0% by weight |
| DMBA | 5.5% by weight |
| Acetophenone | 1.0% by weight |

Recirculation ratio is 26. To the recirculation loop which consists of the CHP cleavage reactors A, B and C 9.3 kg/h of sulfuric acid is fed. The cleavage of technical CHP is carried out at reactor outlet temperatures which are 71° C., 67° C. and 61° C. respectively and at CHP conversions which are 75%, 94%, 98% respectively.

The recycle acetone at the rate of 4444 kg/h calculated by the formula II which was presented in Example 2 is fed to the CHP cleavage unit from vessel 10.

The residence time of reaction products in the DCP cleavage reactor 7 is 640 seconds.

In the mini-reactor 3 of the cleavage unit the value of the temperature drop delta $T_1=0.49°$ C. Value of drop in mini-reactor 12 temperature installed after water supply to the reaction products line at the circulation loop outlet is 1.38° C.

The absolute temperature difference (delta T=delta $T_2$–delta $T_1$) is 0.89° C.

To the product inlet line into the acetone evaporator 8 the aqueous ammonia solution at the concentration of 10% wt and at the rate of 63 kg/h is fed to prevent chemical losses of desired products in the acetone evaporator 8 so that the degree of the conversion of acid into ammonium sulfate in the acetone evaporator is 100%.

As a result the following amounts are produced:

phenol—14610.2 kg/h (yield 99.4%)

acetone—8972.3 kg/h (yield 98.5% )

alphamethylstyrene—56.6 kg/t. of phenol (the yield of AMS is 79.9% theoretical taking into consideration DMBA supply)

the yield of phenol tar—62.51 kg/t of phenol cumene consumption—1335 kg per ton of phenol.

The foregoing examples illustrate the high selectivity of the process at various levels of feed rates of technical CHP under a variety of conditions with excellent reproducibility.

EXAMPLE 8

This example and the examples that follow (Examples 9–14) show an increase in productivity of 2.3 times that of Example 1 by a preferred embodiment of the process of the present invention which uses algorithm (III) for addition of acetone and makes the embodiment efficient and effective over a broad range of concentration of CHP in technical CHP 40–98 wt. %. The process is carried out without changing the equipment layout in comparison with Example 2. All the reactors of the process of the present invention operate under the same pressure that is why all the reactors are connected with each other by top, and the total pressure of the system is 4 kg/cm².

Condensed acetone from vessel 10 is fed to the cleavage unit at a rate of 6890 kg/h calculated by the formula (III):

$$G_{ac} = 0.58 G_{CHP} \times \left( \frac{1.315[CHP]}{50 + 0.25[CHP]} - \frac{2[CHP]}{152} - \frac{[DMBA]}{136} - \frac{[cumene]}{120} - \frac{[AP]}{120} \right)$$

where: $G_{ac}$—acetone amount fed for cleavage in t/hr $G_{CHP}$—technical CHP amount fed for cleavage in t/hr

[CHP]—CHP concentration in technical CHP by weight.

[DMBA]—DMBA concentration in technical CHP by weight

[Cumene]—Cumene concentration in technical CHP by weight

[AP]—Acetophenone (AP) concentration in technical CHP by weight 60 tons per hour of technical CHP are fed to the reactors A, B and C for CHP cleavage. The composition is the same as in Example 1. 21.3 kg/h of sulfuric acid are also fed to the reactors. The cleavage of technical CHP is carried out at a circulation ratio of 26/1 at temperatures at the reactors inlets of 68° C., 67° C. and 60° C. correspondingly and at a CHP conversion of 59%, 94%, 98% correspondingly.

In the mini-reactor 3 of the cleavage unit the value of the temperature drop delta $T_1$=0.4° C.

To the product feed line into reactor 7 of DCP cleavage, water at a rate of 455 kg/h is fed through line 20 and static mixer 19 so that the concentration of the latter in the cleavage products at the reactor outlet would be 1.58 wt % and cleavage time is 485 seconds.

At a point after mixing cleavage products with water there is installed a second mini-reactor (calorimeter) 12, where the value of the drop of temperature delta $T_2$ at outlet and at inlet is measured. And the process control essentially is carried out by means of the value of absolute temperature drop $$\text{delta } T = \text{delta } T_2 - \text{delta } T_1 = 0.62° \text{ C}.$$

To the product inlet line into the acetone evaporator 8 the aqueous ammonia solution at a concentration 10% wt and at a line rate of 141 kg/h is fed through line 18 to exclude chemical losses of desired products in the acetone evaporator 8 so that the degree of conversion of acid to ammonia sulfate is 100% in evaporator 8.

As a result one gets:

phenol—30434.1 kg/h (yield 99.5% )

acetone—18774.8 kg/h (yield 98.5% )

alphamethylstyrene 58.4 kg/t. of phenol (the yield of AMS is 78.9 theoretical % taking into consideration the fed DMBA, yield of phenol tar—54.0 kg/t of phenol cumene consumption—1328 kg per ton of phenol

EXAMPLE 9

This example shows conducting the process of the present invention in reactors of reduced volume with reduced surface of heat transfer and, consequently, with low specific surface of heat transfer. This process is carried out according to the scheme described in Example 8. However, for the apparatus used in this example:

the volume of the reactor system of CHP cleavage is 2.8 times less than in Example 1, the surface of heat transfer of this system is 3.5 times less than in Example 1 and the specific surface of heat exchanger of DCP cleavage is 3 times less than analogous values described in Example 1

26 tons per hour of technical CHP, having the composition defined by Example 1 is fed to reactors A, B & C for CHP cleavage. To the circulating system (process section 1) which consists of reactors A, B and C for CHP cleavage 9.3 kg/h of sulfuric acid is fed. The cleavage of technical CHP is carried out at temperatures at the reactors A, B and C outlet which are 73° C., 70° C. and 65° C. correspondingly and at CHP conversion rates which are 66%, 90%, 96%, correspondingly.

Acetone at a rate of 4312 kg/h calculated based on algorithm III which was presented in Example 8 is fed to the CHP cleavage unit (process section 1) from the vessel 10.

The residence time of reaction products in reactor 7 of DCP cleavage is 630 seconds.

As a result one gets:

phenol—13183.2 kg/h (yield 99.4% )

acetone—8072.5 kg/h (yield 98.8% )

alphamethylstyrene—58,02 kg/ton of phenol (the yield of AMB is 78.4 theoretical % taking into consideration the fed DMBA) yield of phenol tar—55.43 kg/t of phenol Cumene consumption—1329 kg for ton of phenol In the mini-reactor 3 of the cleavage unit the value of the temperature drop delta $T_1$—0.95° C.

The value of the absolute temperature difference $T=\text{delta } T_2-\text{delta } T_1=0.58°$ C.

To the product inlet line of the acetone evaporator 8 an aqueous ammonia solution at a concentration of 10% wt and at a rate of 63 kg/h is fed through line 18 to exclude chemical losses of desired products in the acetone evaporator 8 so that the degree of the conversion of acid into ammonium sulfate in the acetone evaporator 8 is 100%.

EXAMPLE 10

This example illustrates implementation of the process of the present invention in reactors with a heat exchange specific area of 25 m²/t based upon 100% CHP.

26 tons per hour of technical CHP, which has the composition defined by Example 1, is fed to the reactors for CHP cleavage. Circulation ratio is 26. To the circulation loop which consists of reactors A, B and C for CHP cleavage 9.3 kg/h of sulfuric acid is fed. The cleavage of technical CHP is carried out at temperatures at reactors A, B and C outlets of 67° C., 66° C. and 60° C. correspondingly and at a CHP conversion of 62%, 82%, 90% correspondingly.

Acetone at a rate of 4313 kg/h calculated based on algorithm III which is presented in Example 8 is fed to the CHP cleavage unit from vessel 10.

The residence time of reaction products in the reactor 7 of DCP cleavage is 640 seconds.

As a result the following amounts are produced:
phenol—13188.4 kg/h (yield 99.3%)
acetone—8082.9 kg/h (yield 98.8%)
alphamethylstyrene—50.1 kg/ton of phenol (the yield of AMS is 79.8% theor, taking into consideration DMBA supply)
yield of phenol tar—52.9 kg/t of phenol
cumene consumption—1327 kg per ton of phenol In mini reactor 3 of the cleavage unit the value of the temperature drop delta $T_1$–2.17° C. Value of temperature drop in mini-reactor 12 installed after water supply to the reaction products at the circulation loop outlet is 3.11° C.

Absolute temperatures difference (delta T=delta $T_2$–delta $T_1$) is 0.94° C.

To the product inlet line into the acetone evaporator 8 the aqueous ammonia solution at a concentration 10% wt and at a rate of 63 kg/h is fed through line 18 to exclude chemical losses of desired products in the acetone evaporator so that the degree of the conversion of acid into ammonium sulfate in the acetone evaporator is 100%.

EXAMPLE 11

This example illustrates the high selectivity of the process of the present invention at a lower feed rate of technical CHP per cleavage unit and with a higher circulation ratio.

22 tons of technical CHP, which has the composition defined by Example 1, are fed to reactors A, B and C for CHP cleavage. The circulation ratio is 35. To the circulation loop which consists of the reactors A, B and C for CHP cleavage 8.3 kg/h of sulfuric acid is fed. The cleavage of technical CHP is carried out at temperatures at reactors A, B and C outlets which are 72° C., 78° C. and 67° C. correspondingly and at CHP conversion which all 68%, 94%, 98% correspondingly.

Acetone at a rate of 4191.4 kg/h calculated by the formula III which is presented in Example 8, is fed to the CHP cleavage unit (process-section 1) from vessel 10.

The residence time of reaction products in the reactor 7 of DCP cleavage is 737 seconds.

In the mini-reactor 3 of the cleavage unit the value of the temperature drop delta $T_1$=0.39° C. Value of temperature drop in mini-reactor 12 installed after water supply to reaction products at the circulation loop outlet is 0.99° C.

Absolute temperatures difference (delta T=delta $T_2$–delta $T_1$) is 0.6° C.

To the product inlet line into the acetone evaporator 8 the ammonium aqueous solution at a concentration of 10% wt and at a rate of 55.1 kg/h is fed through line 18 to exclude chemical losses of desired products in the acetone evaporator so that the degree of the conversion of acid into ammonium sulfate in the acetone evaporator 8 is 100%.

As a result the following amounts are produced:
phenol—11159,1 kg/h (yield 79,4%)
acetone—6821,8 kg/h (yield 98,5%)
alphamethylstyrene—57,8 kg/ton of phenol (the yield of AMS is 78% theoretical, taking into consideration DMBA supply)
yield of phenol tar—55.6 kg/t of phenol
cumene consumption—1328 kg per ton of phenol

EXAMPLE 12

This Example illustrates the high selectivity of the process of the present invention at an intermediate rate of feed of technical CHP per cleavage unit.

35 tons of technical CHP, which has the composition defined by Example 1, are fed to reactors A, B and C for CHP cleavage. The circulation ratio is 26. To the circulation loop which consists of the reactors A, B and C for CHP cleavage 13.1 kg/h of sulfuric acid is fed. The cleavage of technical CHP is carried out at temperatures at reactors A, B and C outlets which are 73° C., 71° C. and 66° C. correspondingly and at a CHP conversion which is 55%, 82%, 91% correspondingly.

Recycle acetone at the rate of 6410 kg/h calculated based on algorithm III which was presented in Example 8, is fed to the cleavage unit (process section 1) from vessel 10.

The residence time of reaction products in the reactor 7 of DCP cleavage is 467 seconds.

In the mini-reactor 3 of the cleavage unit the value of the temperature drop delta $T_1$=2.09° C. Value of temperatures drop in mini-reactor 12 installed after the water supply to reaction products at the circulation loop outlet is 3.04° C.

Absolute temperatures difference (delta T=delta $T_2$–delta $T_1$) is 0.95° C.

To the product inlet line into the acetone evaporator 8 an aqueous ammonia solution at a concentration of 10% wt and at a rte of 88.7 kg/h is fed to exclude chemical losses of desired products in the acetone evaporator 8 so that the degree of the conversion of acid into ammonium sulfate in the acetone evaporator is 100%.

As a result the following amounts are produced:
phenol—17752.4 kg/h (yield 99.4% )
acetone—10904.3 kg/h (yield 99.1%)
alphamethylstyrene—58.9 kg/t. of phenol (the yield of AMS is 79.67% theor. taking into consideration DMBA supply)

yield of phenol tar—53.84 kg/t of phenol cumene consumption—1328 kg per ton of phenol.

The foregoing Example 12 illustrates the utility of the present invention at a higher level of throughput through CHP cleavage unit (i.e. 35 tons per hour vs. 26 tons per hour).

The following examples illustrate the utility of the present invention with differing concentrations of CHP in the technical CHP feed stream. Example 13 illustrates a feed stream very rich in CHP. Example 14 illustrates a feed stream very lean in CHP.

EXAMPLE 13

This technical CHP example illustrates the high selectivity of the process of the present invention with a higher concentration of CHP.

26 tons of technical CHP, which has the following composition are fed to the reactors A, B and C of CHP cleavage:

| CHP | 91.5% by weight |
| Cumene | 2.0% by weight |
| DMBA | 5.5% by weight |
| Acetophenone | 1.0% by weight |

The circulation ratio is 26. To the circulation loop which consists of the reactors A, B and C for CHP cleavage 9.3 kg/h of sulfuric acid is fed. The cleavage of technical CHP is carried out at temperatures at reactors A, B and C outlets which are 72.5° C. 68° C. and 61° C. correspondingly and at a CHP conversion which is 78%, 96%, 98% correspondingly.

Recycle acetone at a rate of 4444 kg/h calculated based on algorithm III which is presented in Example 8, is fed to the CHP cleavage unit (process section 1) from the vessel 10.

The residence time of reaction products in the reactor 7 of DCP cleavage is 642 seconds.

In the mini-reactor 3 of the cleavage unit the value of the temperature drop delta $T_1$–0.36° C. The value of the temperature drop in mini-reactor 12 installed after water supply to reaction products at circulation loop outlet is 1.46° C.

Absolute temperature difference (delta T=delta $T_2$–delta $T_1$) is 1.1° C.

To the product inlet line into the acetone evaporator 8 an aqueous ammonia solution at a concentration of 10% wt and at a rate of 63 kg/h is fed in exclude chemical losses of desired products in the acetone evaporator 8 so that the degree of the conversion of acid into ammonium sulfate in the acetone evaporator is 100%.

As a result the following amounts are produced:

phenol—14607.4 kg/h (yield 99,3%)

acetone—8975 kg/h (yield 99.9)

alphamethylstyrene—64.8 kg/t of phenol (the yield of AMS is 77.33% theoretical taking into consideration DMBA supply)

yield of phenol tar—69.36 kg/h of phenol cumene consumption—1342 kg per ton of phenol.

EXAMPLE 14

This example illustrates the high selectivity of the process of the present invention with a lower concentration for CHP.

26 tons of technical CHP, which has the following composition are fed to the of CHP cleavage reactors A, B and C:

| CHP | 67% by weight |
| Cumene | 28.6% by weight |
| DMBA | 4% by weight |
| Acetophenone | 0.4% by weight |

The circulation ratio is 26. To the circulation loop which consists of the reactors A, B and C CHP cleavage 11.8 kg/h of sulfuric acid is fed. The cleavage of technical CHP is carried out at temperatures at reactors A, B and C outlets which are 69° C., 63° C. and 62° C. correspondingly and at a CHP conversion which is 68%, 96%, 98% correspondingly.

Recycle acetone at a rate of 2376 kg/h calculated based on algorithm III which is presented in Example 8, is fed to the CHP cleavage unit (process section 1) from vessel 10.

The residence time of reaction products in the reactor of DCP cleavage 7 is 516 seconds.

In the mini-reactor 3 of the cleavage unit the value of the temperature drop delta $T_1$–1.58° C. Value of the temperature drop in mini-reactor 12 installed after water supply to reaction products at circulation loop outlet is 2.04° C.

Absolute temperatures difference (delta T=delta $T_2$–delta $T_1$) is 0.46° C.

To the product inlet line into the acetone evaporator 8 an aqueous ammonia solution at a concentration of 10% wt and at a rate of 79 kg/h is fed through line 18 in exclude chemical losses of desired products in the acetone evaporator 8 so that the degree of the conversion of acid into ammonium sulfate in the acetone evaporator 8 is 100%.

As a result the following amounts are produced:

phenol—14402 kg/h (yield 99,2%)

acetone—8833 kg/h (yield 98.9%)

alphamethylstyrene—67 kg/t of phenol (the yield of AMS is 79,9% theor taking into consideration DMBA supply)

yield of phenol tar—79.9 kg/h of phenol cumene consumption—1331 kg per ton of phenol.

The following is a comparison of the operation of the present invention with the operation of the process of U.S. Pat. No. 5,254,751.

As compared with the process of U.S. Pat. No. 5,254,751 the cleavage process of the present invention proceeds at a faster rate and is more "robust". The three reactors A, B and C in the process of the present invention are smaller and operate at higher temperatures (and higher pressure to suppress boiling).

| | ----Temp C---- | | | |
| | A | B | C | Pressure |
|---|---|---|---|---|
| present invention | 68–79 | 78–65 | 69–60 | 3–4 atm |
| U.S. Pat. No. 5,254,751 | 50–62 | 62–57 | 57–50 | 1 atm |

CHP conversion profile across the three reactors is different from that of 5,254,751. In the present invention a much higher percentage of the CHP feed is reacted away in the first reactor A. And essentially no unreacted CHP is allowed to exit reactor C. The delta $T_1$ calorimeter is controlled at a very low value: (<1 degree).

|  | % CHP Conversion | | | wt % CHP |
| --- | --- | --- | --- | --- |
|  | A | B | C | Calorimeter 3 |
| present invention | 75 | 90 | 98 | 0.2 |
| U.S. Pat. No. 5,254,751 | 45 | 75 | 88 | 1.0 |

In the present process a higher circulation rate (26:1–40:1) in the A, B and C reactors is employed to give additional dilution of CHP feed so that safety is maintained at the faster cleavage rate. In the CHP concentration feeding reactor A is 2.5–3 wt % as opposed to 4.5–5 wt % with the 5,254,751 process. CHP residence time in stage 1 of the present process is 17–28 sec compared with 50–60 sec in the 5,254,751 process.

For the first stage reaction, sulfuric acid, water and acetone concentrations are essentially the same in both processes. Sulfuric catalyst conc is 300 ppm in both cases.

In the present process the first and second stage vents are tied together so that both steps operate at identical elevated pressures. This saves investment in pumps and auxiliary equipment.

The foregoing examples and experimental and predictive results are meant to explain and describe the invention, and are not intended to limit the invention to only those parameters specifically disclosed. Thus, upon perusing this specification, various modifications of the foregoing description may become apparent, and such are intended to be within the scope and spirit of the invention as defined by the following claims.

The data from the examples is summarized in the table below.

| EXAMPLE # | Loading of technical CHP t/hr | Reaction volume of cleavage reactors | | Heat-exchange area and total specific area | | Residence time in cleavage reactors | | Circulation ratio | Recycled acetone flow rate kg/hr | Temperature in cleavage reactors | | | DCP 7 |
| --- | --- | --- | --- | --- | --- | --- | --- | --- | --- | --- | --- | --- | --- |
|  |  | CHP m³ | DCP | m² | m²/t of CHP | CHP sec. | DCP sec. |  |  | A | B | C | °C. |
| 1 | 26 | 10.08 | 16 | 1254 | 58 | 74 | 2040 | 16 | 5492 | 58 | 55 | 50 | 93 |
| 2 | 60 | 10.08 | 16 | 1254 | 25 | 21.4 | 485 | 26 | 6893 | 68 | 67 | 60 | 99 |
| 3 | 26 | 3.6 | 7 | 360 | 17 | 18 | 638 | 26 | 4312 | 79 | 75 | 69 | 95 |
| 4 | 26 | 4.5 | 7 | 540 | 25 | 22 | 640 | 26 | 4312 | 67 | 66 | 61 | 96 |
| 5 | 22 | 4.5 | 7 | 540 | 25 | 28 | 865 | 35 | 4192 | 72 | 78 | 67 | 93 |
| 6 | 35 | 4.5 | 7 | 540 | 19 | 16.8 | 487 | 26 | 4821 | 74 | 71 | 65 | 96 |
| 7 | 26 | 4.5 | 7 | 540 | 23 | 22 | 640 | 26 | 4444 | 71 | 67 | 61 | 94 |
| 8 | 60 | 10.08 | 16 | 1234 | 25 | 21 | 485 | 26 | 6898 | 68 | 67 | 69 | 99 |
| 9 | 26 | 3.8 | 7 | 360 | 17 | 18 | 638 | 26 | 4312 | 73 | 70 | 65 | 95 |
| 10 | 26 | 4.5 | 7 | 540 | 25 | 22 | 640 | 26 | 4313 | 67 | 65 | 63 | 96 |
| 11 | 22 | 4.5 | 7 | 540 | 25 | 28 | 737 | 35 | 4191 | 72 | 78 | 67 | 93 |
| 12 | 35 | 4.5 | 7 | 540 | 19 | 16.8 | 467 | 26 | 6410 | 73 | 71 | 65 | 96 |
| 13 | 26 | 4.5 | 7 | 540 | 23 | 22 | 640 | 26 | 4444 | 72 | 68 | 61 | 94 |
| 14 | 26 | 4.5 | 7 | 540 | 23 | 22 | 516 | 26 | 2376 | 69 | 63 | 62 | 96 |

| EXAMPLE # | CHP conversion in reactors % | | | Temperature difference in mini-reactors °C. | | Temperature difference between mini-reactors °C. | $H_2SO_4$ neutralization degree in DCP cleavage reactor % | Water concentration in DCP cleavage reactor wt. % | AMS yield after DCP cleavage reactor % theo. | AMS yield after evaporator % theo. |
| --- | --- | --- | --- | --- | --- | --- | --- | --- | --- | --- |
|  | A | B | C | 1st | 2nd |  |  |  |  |  |
| 1 | 38 | 73 | 85 | 5.6 | — | — | 25 | 1.38 | 80.3 | 73.4 |
| 2 | 62 | 96 | 98 | 0.40 | 1.05 | 0.65 | 100 | 1.63 | 79.9 | 79.9 |
| 3 | 77 | 96 | 98 | 0.34 | −1.0 | 0.56 | 100 | 1.68 | 78.8 | 78.8 |
| 4 | 62 | 87 | 94 | 1.26 | 1.98 | 0.72 | 100 | 1.55 | 79.9 | 79.9 |
| 5 | 65 | 92 | 97 | 0.82 | 1.68 | 0.86 | 100 | 1.68 | 79.3 | 79.3 |
| 6 | 70 | 93 | 97 | 0.64 | 1.91 | 1.27 | 100 | 1.58 | 79.6 | 79.6 |
| 7 | 75 | 94 | 98 | 0.49 | 1.38 | 0.89 | 100 | 1.67 | 79.6 | 79.6 |
| 8 | 59 | 94 | 98 | 0.40 | 1.58 | 0.62 | 100 | 1.58 | 78.9 | 78.9 |
| 9 | 66 | 90 | 96 | 0.95 | 1.53 | 0.58 | 100 | 1.68 | 78.4 | 78.4 |
| 10 | 62 | 82 | 90 | 2.17 | 3.11 | 0.94 | 100 | 1.55 | 79.8 | 79.8 |
| 11 | 68 | 94 | 98 | 0.39 | 0.99 | 0.6 | 100 | 1.68 | 78.0 | 78.0 |
| 12 | 55 | 82 | 91 | 2.09 | 3.04 | 0.95 | 100 | 1.58 | 79.6 | 79.6 |
| 13 | 78 | 96 | 98 | 0.36 | 1.46 | 1.10 | 100 | 1.67 | 77.3 | 77.3 |
| 14 | 68 | 96 | 98 | 1.58 | 2.04 | 0.40 | 100 | 1.50 | 79.9 | 79.5 |

In Example 1, the pressure in CHP cleavage reactors A, B and C is atmospheric and the pressure in DCP cleavage reactor 7 is 3 atmospheres.
In Examples 2–14, the pressure in CHP cleavage reactors A, B and C as well as DCP cleavage reactor 7 is 4 atmospheres.

We claim:

1. An improved method for the production of phenol and acetone from cumene comprising the acid-catalyzed cleavage of technical cumylhydroperoxide and the cleavage of dicumylperoxide wherein the improvement comprises cleaving the technical cumylhydroperoxide in a first vessel to obtain a cumylhydroperoxide cleavage mass comprising dicumylperoxide and cleaving the dicumylperoxide in a second vessel at the same pressure above atmospheric pressure whereby no pumps and surge vessels are required to move the cumylhydroperoxide cleavage mass from the cumylhydroperoxide cleavage vessel to the dicumyl peroxide cleavage vessel.

2. The method of claim 1 wherein the pressure in the cumylhydroperoxide cleavage and dicumylperoxide cleavage vessels is from about 2 to about 10 atmospheres.

3. The method of claim 2 wherein the pressure is from about 3 to about 5 atmospheres.

4. The method of claim 1 wherein the cumylhydroperoxide is cleaved in a multiplicity of vessels which are circulating reactors of a shell and tube design connected in series and the dicumylperoxide is cleaved in a single vessel which is a plug flow reactor.

5. The method of claim 4 wherein the cumylhydroperoxide is cleaved in three :reactors with a temperature profile as follows:

first reactor—from about 57° C. to about 82° C.

second reactor—from about 65° C. to about 82° C.

third reactor—from about 57° C. to about 70° C.

6. The method of claim 5 wherein the temperature profile is first reactor—from about 60° C. to about 79° C.

second reactor—from about 63° C. to about 78° C.

third reactor—from about 60° C. to about 69° C.

7. The method of claim 1 wherein after the second vessel the pressure is reduced to about atmospheric pressure or below and acetone which is present in the cleavage mass is partially evaporated, condensed and returned to the first vessel and before the acetone is partially evaporated but after the cleavage mass leaves the second vessel aqueous ammonia is added to the cleavage mass whereby the residual acid catalyst is converted to its neutral salt.

8. The method of claim 1 wherein the technical cumylhydroperoxide feed is from about 74 percent by weight to about 92 percent by weight cumylhydroperoxide and acetone is recycled to the cumylhydroperoxide cleavage vessel according to the following algorithm:

$$G_{ac} = G_{CHP} \times 0.125[CHP] + \frac{35}{G_{CHP}[CHP]}$$

wherein: $G_{ac}$ is acetone amount fed for cleavage in t/hr, $G_{CHP}$ is technical cumylhydroperoxide amount fed for cleavage, t/hr and

[CHP] is cumylhydroperoxide concentration in technical cumylhydroperoxide by weight.

9. The method of claim 1 wherein the cumylhydroperoxide cleavage mass is from 40 to 98% by weight cumylhydroperoxide and acetone is recycled to the cumyl hydroperoxide cleavage vessel according to the following algorithm:

$$G_{ac} = 0.58 G_{CHP} \times \left( \frac{1.315[CHP]}{50 + 0.25[CHP]} - \frac{2[CHP]}{152} - \frac{[DMBA]}{136} - \frac{[cumene]}{120} - \frac{[AP]}{120} \right)$$

where: $G_{ac}$ is acetone amount fed for cleavage in t/hr $G_{CHP}$ is technical cumylhydroperoxide amount fed for cleavage in t/hr,

[CHP] is cumylhydroperoxide concentration in technical cumyl by weight,

[DMBA] is dimethylbenzyl alcohol concentration in technical cumylhydroperoxide by weight,

[Cumene] is cumene concentration in technical cumylhydroperoxide by weight and

[AP] is acetophenone concentration in technical cumylhydroperoxide by weight.

10. The method of claim 1 wherein a portion of the cumylhydroperoxide cleavage mass is recycled to the cumylhydroperoxide vessel through a recycle line and connected to, and in parallel with, the recycle line is a first calorimeter having an inlet and an outlet through which a portion of the recycled cumylhydroperoxide cleavage mass passes and the temperature of the portion is measured at the inlet to the first calorimeter and at the outlet of the first calorimeter to give a first temperature differential and a second calorimeter having an inlet and an outlet is connected to, and in parallel with, a line connecting the cumylhydroperoxide cleavage vessel to the dicumylperoxide catalyst cleavage vessel after a point in the line at which water has been added to the cumylhydroperoxide cleavage mass through which inlet and outlet of said second calorimeter a portion of the cumylhydroperoxide cleavage mass moving to the dicumylperoxide cleavage vessel passes and the temperature of the portion is measured at the inlet to the second calorimeter and at the outlet of the second calorimeter to give a second temperature differential and the absolute difference between the first and second differential, i.e., absolute delta T=delta $T_2$–delta $T_1$, is within the range of about 0.2° C. to about 3° C.

11. The method of claim 1 wherein a portion of the cumylhydroperoxide cleavage mass is recirculated through the first vessel at a ratio of from about 20 to about 40 parts by weight of recirculated cleavage mass to one part by weight of fed cumene hydroperoxide.

12. The method of claim 11 wherein the ratio is from about 26 to about 35 parts by weight of recirculated cleavage mass to one part by weight of fed cumene hydroperoxide.

* * * * *